(12) United States Patent
Udagawa et al.

(10) Patent No.: US 8,383,391 B2
(45) Date of Patent: Feb. 26, 2013

(54) MUTANT CELL WITH DELETED OR DISRUPTED GENES ENCODING PROTEASE

(75) Inventors: Hiroaki Udagawa, Kanajawa (JP); Christian Isak Jørgensen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 175 days.

(21) Appl. No.: 12/678,891

(22) PCT Filed: Sep. 30, 2008

(86) PCT No.: PCT/EP2008/063102
§ 371 (c)(1), (2), (4) Date: Jun. 28, 2010

(87) PCT Pub. No.: WO2009/043854
PCT Pub. Date: Apr. 9, 2009

(65) Prior Publication Data
US 2010/0304433 A1   Dec. 2, 2010

Related U.S. Application Data

(60) Provisional application No. 60/977,235, filed on Oct. 3, 2007.

(30) Foreign Application Priority Data

Oct. 1, 2007 (EP) ..................... 07117588

(51) Int. Cl.
*C12N 1/20* (2006.01)
(52) U.S. Cl. .................... 435/252.3
(58) Field of Classification Search .......... None
See application file for complete search history.

(56) References Cited

U.S. PATENT DOCUMENTS

2005/0054071 A1   3/2005   Udagawa
2005/0055747 A1   3/2005   Lassen et al.

FOREIGN PATENT DOCUMENTS

| WO | WO 89/06270 | 7/1989 |
|---|---|---|
| WO | WO 94/25583 | 11/1994 |
| WO | WO 97/35956 | 10/1997 |
| WO | WO 98/12300 | 3/1998 |
| WO | WO 01/38637 | 5/2001 |
| WO | WO 2006/110677 | 10/2006 |
| WO | WO 2007/045248 | 4/2007 |

OTHER PUBLICATIONS

Pel et al, Genome sequencing and analysis of the versatile cell factory *Aspergillus niger* CBS 513.88. Nat. Biotechnol. 25 (2), 221-231 (Jan. 28, 2007).*
GenBank Acc# XP_001388580 from Pel et al, Nat. Biotechnol. 25 (2), 221-231 (Jan. 28, 2007). Alignment with SEQ ID No. 5.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
MEROPS database; cleavage of XXX-LEU-LEU↓VAL-TYR; May 15, 2012.*
Herman et al., "Genome sequencing and analysis of the versatile cell factory *Aspergillus niger* CBS 513.88", Nature Biotechnology, vol. 25, No. 2, pp. 221-231 (2007).
Database UNIPROT A2Q7N9, "Similarity to hypothetical protein encoded by slr0318—*Synechocystis* sp", (2007).
Database EMBL: AM269954, "*Aspergillus niger* contig An01c0070, complete genome" (2007).
Search Report issued in corresponding international application No. PCT/EP2008/063102 dated Dec. 3, 2008.
Saupe et al., Database GenBank—Access No. CAK43512.1 (2007).

\* cited by examiner

*Primary Examiner* — Sheridan Swope
(74) *Attorney, Agent, or Firm* — Michael W. Krenicky

(57) ABSTRACT

This disclosure relates to mutant cells with deleted or disrupted genes encoding protease(s).

8 Claims, 4 Drawing Sheets lane 1: LMW Marker (97, 66, 45, 30, 20, 14.4 kDa, GE Healthcare))
lane 2: Purified Proteases (Boiled)
lane 3: Purified Proteases (without boiling and 2-Mercaptoethanol)
Skim milk-agarose over lay

Figure 2

*Aspergillus niger* 19 kDa protease DNA sequence and protein sequence

```
  M   S   P       I   P   S   Y       S   R   P       G   R   G   Q       H   F   Q
ATGTCCCCAA TCCCCAGCTA CTCCCGCCCC GGCCGCGGCC AACACTTCCA

D   A   Y       G   F   A       E   A   C   I       A   G   D       R   M   E
AGATGCCTAC GGCTTCGCCG AAGCCTGCAT AGCCGGAGAC CGAATGGAAA

I   A   G   Q
TAGCCGGCCA GAGTGAGCCA CCATCTCCTT TCCCTCCATT TCCCTCATCA

T   G   M       S   P   T
CCAACTAATC CAATCCCCCC CTCAACAAAC TAGCCGGCAT GTCCCCCACA

S   T   E       V   P   P   T       L   E   E       E   V   A       Q   A   F   N
TCAACCGAAG TCCCACCCAC CCTCGAAGAA GAAGTCGCGC AAGCATTCAA

N   I   N       E   V   I       L   Y   T   L       E   K   A       K   P   D
CAACATCAAC GAAGTTATCC TCTACACACT AGAGAAAGCC AAGCCCGATC

L   R   A   S       V   K   S       G   W   D       R   V   V   K       I   R   T
TGCGCGCTAG CGTCAAGAGC GGCTGGGACC GCGTCGTGAA GATCCGCACG

Y   H   V       Q   L   P   Q       T   R   E       K   I   I       G   L   M   V
TACCATGTCC AGTTGCCCCA GACCCGGGAG AAGATTATCG GCCTAATGGT

E   N   V       K   K   W       C   P   D   H       Q   P   T       W   T   M
AGAGAATGTT AAGAAGTGGT GTCCGGATCA TCAGCCTACT TGGACTATGT

L   G   I   E       A   L   P       F   E   G       Q   N   L   E       I   E   V
TGGGGATTGA GGCCTTGCCG TTTGAAGGGC AGAATTTGGA GATTGAGGTG

D   V   F   L       G  stop
GATGTTTTCT TGGGGTGA
```

Figure 3. Gel permeation Chromatography of 19 kDa protease
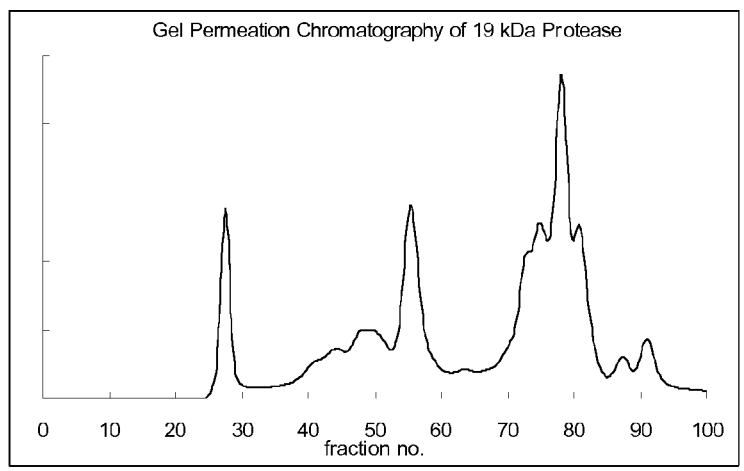
Figure 4. SDS-PAGE chromatography of selected fractions
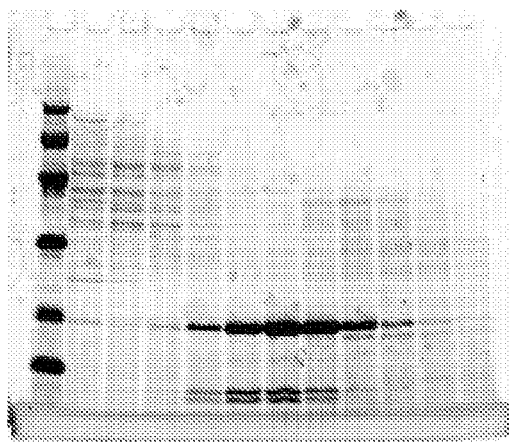
from the left
1: Low Molecular Weight Marker
 (GE healthcare)
2: fraction 51   8: fraction 57
3: fraction 52   9: fraction 58
4: fraction 53   10: fraction 59
5: fraction 54   11: fraction 60
6: fraction 55   12: fraction 61
7: fraction 56

Figure 5. pH profile of the 19 kDa protease
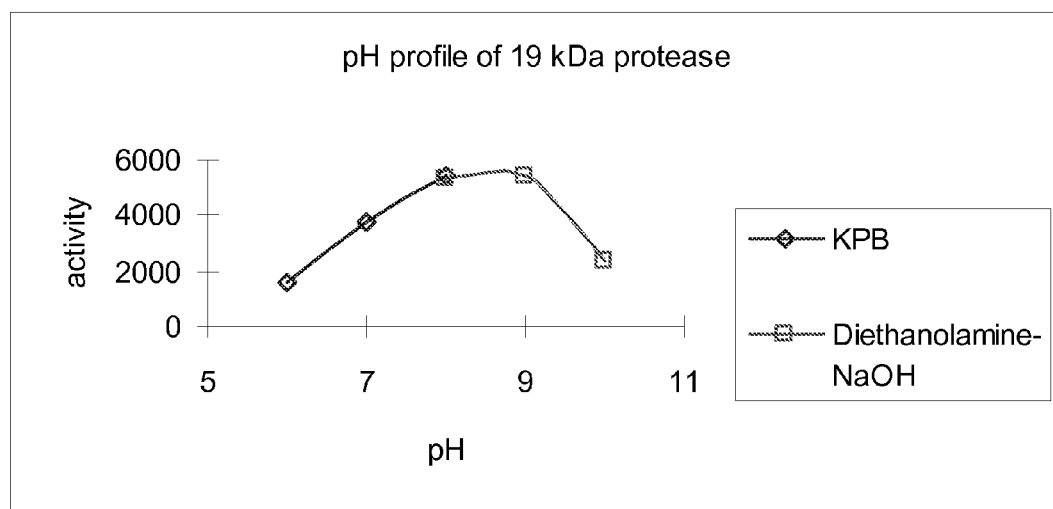

US 8,383,391 B2

MUTANT CELL WITH DELETED OR DISRUPTED GENES ENCODING PROTEASE

CROSS-REFERENCE TO RELATED APPLICATIONS

This application is a 35 U.S.C. 371 national application of PCT/EP2008/063102 filed Sep. 30, 2008, which claims priority or the benefit under 35 U.S.C. 119 of European application no. 07117588 filed Oct. 1, 2007 and U.S. provisional application No. 60/977,235 filed Oct. 3, 2007, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to isolated polypeptides having protease activity and isolated polynucleotides encoding the polypeptides. The invention also relates to nucleic acid constructs, vectors, and host cells comprising the polynucleotides as well as methods for producing and using the polypeptides.

BACKGROUND OF THE INVENTION

It is an object of the present invention to provide polypeptides having protease activity and polynucleotides encoding the polypeptides.

In the detergent industry enzymes have for more than 30 years been implemented in washing formulations. Enzymes used in such formulations comprise proteases, lipases, amylases, cellulases, mannosidases as well as other enzymes or mixtures thereof. Commercially most important enzymes are proteases.

WO 89/06270 (Novozymes A/S) discloses a detergent composition comprising a protease with a narrow substrate specificity, namely a trypsin-like protease capable of cleaving peptide bonds at C-terminal side of lysine or arginine.

Further WO 94/25583 discloses the cloning of a DNA sequence encoding a Fusarium trypsin-like protease and obtaining expression of an active trypsin-like protease from said DNA-sequence.

However, even though a number of useful proteases and protease variants have been described, there is still a need for further improvement of proteases or protease variants for a number of industrial uses.

In particular, the problem of maintaining high activity in the presence of other components of typical detergent compositions tends to reduce the performance of proteases.

Therefore, an object of the present invention is to provide new proteases, which are suitable for use in detergents for the use in for example laundry and/or cleaning of hard surfaces.

Fungi, and especially filamentous fungi, are widely used commercially because of their ability to secrete remarkably high levels of proteins.

Among the filamentous fungi species belonging to the genus *Aspergillus* have a long history of commercial use for the production of endogenous and heterologous proteins.

One disadvantage with most microorganisms used for the production of proteins is the inherent production of proteases which may subject a protein product of interest to degradation due to proteolysis.

Various ways of avoiding this have been envisaged. Among other solutions it has been suggested to delete or disrupt the genes encoding the various proteases.

WO 2006/110677 discloses recombinant fungal host cell belonging to the species *Aspergilus niger*, wherein the chromosomal genes derA, derB, htmA, mnn9, mnn10, ochA, pepAa, pepAb, pepAc, pepAd, pepF and combination had been inactivated in order to reduce degradation of heterologously produced proteins.

Unfortunately, some fungi produce a high number of different proteases.

A need is therefore persisting for strains of filamentous fungi exhibiting no or very low levels of protease production.

SUMMARY OF THE INVENTION

The present invention relates to an isolated protease having an amino acid sequence which has at least 95% identity with amino acids 2 to 148 of SEQ ID NO: 5.

The present invention also relates to methods for producing such polypeptides having protease activity comprising (a) cultivating a recombinant host cell comprising a nucleic acid construct comprising a polynucleotide encoding the polypeptide under conditions conducive for production of the polypeptide; and (b) recovering the polypeptide.

The present invention also relates to a cleaning or detergent composition, preferably a laundry or dish wash composition, comprising the protease according to the invention.

Further aspects of the present invention relate to use of the proteases according to the invention in a cleaning or detergent composition; a method for cleaning or washing a hard surface or laundry comprising contacting the hard surface or the laundry with the composition of the invention The present invention also relates to fungi, modified so that the expression of the protease of the invention have been reduced or completely abolished compared to the corresponding not modified fungi. Preferably the modification has been performed using recombinant DNA technology.

Thus the invention furthermore relates to methods for producing such fungi, obtained by deletion of at least a part of polynucleotides encoding polypeptides having protease activity, selected from the group consisting of:

(a) a polynucleotide encoding a polypeptide having an amino acid sequence which has at least 60%, such as at least 65%, such as at least 70%, such as at least 75%, such as at least 80%, such as at least, 85%, such as at least, 90%, such as at least, 95%, such as at least 95%, such as at least 96%, such as at least 97%, such as at least 98%, such as at least 99%, such as at least 99.5% identity with amino acids 2 to 148 of SEQ ID NO: 5;

(b) a polynucleotide which hybridizes under at least medium stringency conditions with nucleotides 1 to 515 of SEQ ID NO: 4, or a complementary strand thereof.

This may be obtained through a method comprising:
i) cloning of a polynucleotide encoding a polypeptide having protease activity, selected from the group consisting of:
  (a) a polynucleotide encoding a polypeptide having an amino acid sequence which has at least 60%, such as at least 65%, such as at least 70%, such as at least 75%, such as at least 80%, such as at least, 85%, such as at least, 90%, such as at least, 95%, such as at least 95%, such as at least 96%, such as at least 97%, such as at least 98%, such as at least 99%, such as at least 99.5% identity with amino acids 2 to 148 of SEQ ID NO: 5;

(b) a polynucleotide which hybridizes under at least medium stringency conditions with nucleotides 1 to 515 of SEQ ID NO: 4, or a complementary strand thereof;
from a fungus of interest, ii) producing DNA constructs comprising the polynucleotide cloned in i) wherein an internal part has been substituted, deleted, or extra DNA has been inserted, iii) transforming said fungus with the constructs, and iv) isolating transformants which express an reduced amount of the protease of the invention, compared to the amount expressed by the not modified fungus.

Further, the invention also related to methods for producing fungi where the expression of the protease of the invention has been reduced compared to the unmodified parent fungi, where the expression has been reduced using the well-known anti-sense technology, by constructing a vector that upon introduction into said fungi gives rise to synthesis of a RNA-molecule complementary the mRNA transcribed from polynucleotides encoding polypeptides having protease activity, selected from the group consisting of:

(a) a polynucleotide encoding a polypeptide having an amino acid sequence which has at least 60%, such as at least 65%, such as at least 70%, such as at least 75%, such as at least 80%, such as at least, 85%, such as at least, 90%, such as at least, 95%, such as at least 95%, such as at least 96%, such as at least 97%, such as at least 98%, such as at least 99%, such as at least 99.5% identity with amino acids 2 to 148 of SEQ ID NO: 5;

(b) a polynucleotide which hybridizes under at least medium stringency conditions with nucleotides 1 to 515 of SEQ ID NO: 4, or a complementary strand thereto.

The invention furthermore relates to DNA constructs intended for use in the above mentioned methods.

Furthermore the invention relates to methods of producing a desired protein or gene product, especially secreted proteins, whereby a fungal host modified and optionally transformed with a DNA construct comprising at least a DNA sequence coding for the protein or gene product of interest, is cultivated in a suitable growth medium at appropriate conditions and the desired gene product is recovered and purified.

When working with the invention it was surprisingly found that the fungi of the invention produces such secreted proteins in a much improved yield. In particular it has been found that the polypeptide of the invention appears to be responsible for cleaving a CBM (carbohydrate binding module) from a polypeptide comprising a catalytic part and a CBM, and that host cells in which the expression of the polypeptide of the invention has been reduced gives rise to less cleaving of the CBM compared with the same host cell but where the expression of the polypeptide of the invention has not been reduced.

Thus another aspect of the invention relates to a method for producing a protein product comprising a polypeptide comprising two or more domains of which one domain is carbon hydrate binding module, wherein the method comprises the steps of, a) fermentation of a cell having reduced expression of the polypeptide according to any of the claims 1-2, which cell produces said polypeptide comprising two or more domains, and b) recovering the product.

In a further the invention also relates methods for producing protein product essentially free of the protease activity of the polypeptide according to the invention, such as a method comprising the steps of, a) fermentation of a cell expressing a polypeptide according to any of the claims 1-8 as well as a protein product of interest, b) adding agent capable of inhibiting protease activity of a polypeptide according to the invention to the fermentation broth before, during or after the fermentation has been completed, and c) recovering product of interest from fermentation broth.

Or a method comprising the steps of a) cultivating a cell under conditions permitting expression of said protein product, b) subjecting the culture to combined pH and temperature treatment, and c) recovering the product.

BRIEF DESCRIPTION OF THE FIGURES

FIG. 2 shows the genomic DNA sequence and the deduced amino acid sequence of an *Aspergillus niger* 19 kDa protease (SEQ ID NOs: 4 and 5, respectively).

FIG. 3 shows a gel permeation chromatography of an *A. oryzae* transformed with an expression plasmid comprising the polynucleotide of the invention.

FIG. 4 shows a SDS-PAGE gel loaded with selected fraction of the gel permeation chromatography disclosed in FIG. 3.

FIG. 5 shows the pH profile of the protease having SEQ ID NO: 3

DEFINITIONS

Figure 1:
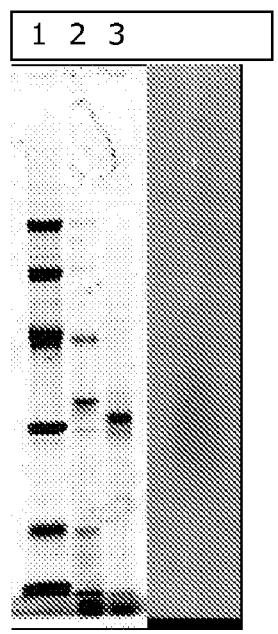
FIG. 1 shows a SDS-PAGE gel showing the purified 19 kDa protease of the invention, as described in Example 1.

Protease activity: The term "protease activity" is defined herein as a proteolytic activity which catalyzes the hydrolysis of the peptide bond connecting two amino acids in a peptide. For purposes of the present invention, protease activity is determined according to the procedure described by S. Ishiura, et al, FEBS Lett., 189, 119 (1985)]. One unit of protease activity is defined as 1.0 µmole of [aminomethylcoumarin] liberated from substrate Suc-LLVY-MCA (available at Peptide Inc. (Osaka, Japan)) per minute at 37° C., pH 6.7.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the protease activity of the polypeptide consisting of the amino acid sequence shown as amino acids 2 to 148 of SEQ ID NO: 5.

Isolated polypeptide: The term "isolated polypeptide" as used herein refers to a polypeptide that is removed from at least one component with which is natively associated. The term as used herein refer to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences is described by the parameter "identity".

For purposes of the present invention, the alignment of two amino acid sequences is determined by using the Needle program from the EMBOSS package version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"); e.g. amino acids 2-148 of SEQ ID NO: 5 and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "|"). The length of a sequence is the number of amino acid residues in the sequence (e.g. the length of SEQ ID NO: 5 is 148).

In the purely hypothetical alignment example below, the overlap is the amino acid sequence "HTWGER-NL" of Sequence 1; or the amino acid sequence "HGWGEDANL" of Sequence 2. In the example a gap is indicated by a "-".

Hypothetical alignment example:

```
Sequence 1: ACMSHTWGER-NL
                | ||| ||
Sequence 2:     HGWGEDANLAMNPS
```

For purposes of the present invention, the degree of identity between two nucleotide sequences is determined by the Wilbur-Lipman method (Wilbur and Lipman, 1983, Proceedings of the National Academy of Science USA 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

In a particular embodiment, the percentage of identity of an amino acid sequence of a polypeptide with, or to, amino acids 2 to 148 of SEQ ID NO: 5 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage.

Polypeptide Fragment: The term "polypeptide fragment" is defined herein as a polypeptide having one or more amino acids deleted from the amino and/or carboxyl terminus of SEQ ID NO: 5 or a homologous sequence thereof, wherein the fragment has protease activity.

Subsequence: The term "subsequence" is defined herein as a nucleotide sequence having one or more nucleotides deleted from the 5' and/or 3' end of SEQ ID NO: 4 or a homologous sequence thereof, wherein the subsequence encodes a polypeptide fragment having protease activity. Preferably, a subsequence contains at least 100 nucleotides, more preferably at least 200 nucleotides, and most preferably at least 300 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the polypeptide consisting of the amino acids 2 to 148 of SEQ ID NO: 5 as well as genetic manipulation of the DNA encoding that polypeptide. The modification(s) can be substitution(s), deletion(s) and/or insertions(s) of the amino acid(s) as well as replacement(s) of amino acid side chain(s).

Artificial variant: When used herein, the term "artificial variant" means a polypeptide having protease activity produced by an organism expressing a modified nucleotide sequence of SEQ ID NO: 4. The modified nucleotide sequence is obtained through human intervention by modification of the nucleotide sequence disclosed in SEQ ID NO: 4.

DETAILED DESCRIPTION OF THE INVENTION

Polypeptides Having Protease Activity

In a first aspect, the present invention relates to isolated polypeptides having an amino acid sequence which has a degree of identity to amino acids 2 to 148 of SEQ ID NO: 5 (i.e., the mature polypeptide) of at least 95%, such as preferably 96%, such as preferably at least 97%, such as preferably 98%, such as preferably 99% and such as preferably 99.5% which have protease activity (hereinafter "homologous polypeptides"). In a preferred aspect, the homologous polypeptides have an amino acid sequence which differs by five amino acids, preferably by four amino acids, more preferably by three amino acids, even more preferably by two amino acids, and most preferably by one amino acid from amino acids 2 to 148 of SEQ ID NO: 5.

A polypeptide of the present invention preferably comprises the amino acid sequence of SEQ ID NO: 5 or an allelic variant thereof; or a fragment thereof that has protease activity. In a preferred aspect, a polypeptide comprises the amino acid sequence of SEQ ID NO: 5. In another preferred aspect, a polypeptide comprises amino acids 2 to 148 of SEQ ID NO: 5, or an allelic variant thereof; or a fragment thereof that has protease activity. In another preferred aspect, a polypeptide comprises amino acids 2 to 148 of SEQ ID NO: 5. In another preferred aspect, a polypeptide consists of the amino acid sequence of SEQ ID NO: 5 or an allelic variant thereof; or a fragment thereof that has protease activity. In another preferred aspect, a polypeptide consists of the amino acid sequence of SEQ ID NO: 5. In another preferred aspect, a polypeptide consists of amino acids 2 to 148 of SEQ ID NO: 5 or an allelic variant thereof; or a fragment thereof that has protease activity. In another preferred aspect, a polypeptide consists of amino acids 2 to 148 of SEQ ID NO: 5.

The nucleotide sequence of SEQ ID NO: 4 or a subsequence thereof, as well as the amino acid sequence of SEQ ID NO: 5 or a fragment thereof, may be used to design a nucleic acid probe to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labelled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having protease activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 4 or a subsequence thereof, the carrier material is used in a Southern blot.

For purposes of the present invention, hybridization indicates that the nucleotide sequence hybridizes to a labelled nucleic acid probe corresponding to the nucleotide sequence shown in SEQ ID NO: 4, its complementary strand, or a subsequence thereof, under medium to very high stringency conditions. Molecules to which the nucleic acid probe hybridizes under these conditions can be detected using X-ray film.

For long probes of at least 100 nucleotides in length, medium to very high stringency conditions are defined as prehybridization and hybridization at 42° C. in 5×SSPE, 0.3% SDS, 200 μg/ml sheared and denatured salmon sperm DNA, and either 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 55° C. (medium stringency), more preferably at least at 60° C. (medium-high stringency), even more preferably at least at 65° C. (high stringency), and most preferably at least at 70° C. (very high stringency).

In a particular embodiment, the wash is conducted using 0.2×SSC, 0.2% SDS preferably at least at 55° C. (medium stringency), more preferably at least at 60° C. (medium-high stringency), even more preferably at least at 65° C. (high stringency), and most preferably at least at 70° C. (very high stringency). In another particular embodiment, the wash is conducted using 0.1×SSC, 0.2% SDS preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

Effective $T_m$=81.5+16.6(log M[Na$^+$])+0.41(% G+C)−0.72(% formamide)

The G+C content of SEQ ID NO: 4 or nucleotides 1 to 518 of SEQ ID NO: 4 is 55%. For medium stringency, the formamide is 35% and the Na$^+$ concentration for 5×SSPE is 0.75 M. Applying this formula to these values, the Effective $T_m$ is 77° C.

Another relevant relationship is that a 1% mismatch of two DNAs lowers the $T_m$ by 1.4° C. To determine the degree of identity required for two DNAs to hybridize under medium stringency conditions at 42° C., the following formula is used:

% Homology=100−[(Effective $T_m$−Hybridization Temperature)/1.4]

Applying this formula to the values, the degree of identity required for two DNAs to hybridize under medium stringency conditions at 42° C. is 100−[(77−42)/1.4]=75%.

In a second aspect, the present invention relates to isolated polypeptides having protease activity encoded by a polynucleotide comprising nucleotides 1 to 515 of SEQ ID NO: 4, as a unique motif.

In a fourth aspect, the present invention relates to isolated polypeptides having the following physicochemical properties:

a pH optimum between 8 and 9;
a molecular weight about 19 kDa;
not inhibited by leupeptin, pepstatin, 4-(2-aminoethyl)-benzenesulfonyl fluoride (AEBSF), ZnSO$_4$ and EDTA;
having high activity on the substrate Suc-LLVY-MCA and low activity on the substrates: Glt-AAF-MCA, Boc-FSR-MCA, Suc(OMe)-AAPV-MCA and Z-LLE-MCA.

In a third aspect, the present invention relates to artificial variants comprising a conservative substitution, deletion, and/or insertion of one or more amino acids of SEQ ID NO: 5 or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physical-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., protease activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30:10832-10837; U.S. Pat. No. 5,223,409; WO 92/06204), and region-directed mutagenesis (Derbyshire et al., 1986, Gene 46:145; Ner et al., 1988, DNA 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids 2 to 148 of SEQ ID NO: 5 is at most 6, preferably at most 5, more preferably 4, even more preferably 3, most preferably 2, and even most preferably 1.
Sources of Polypeptides Having Protease Activity A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Aspergillus, Aureobasidium, Cryptococcus, Filobasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having protease activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide.

In another preferred aspect, the polypeptide is an *Aspergillus, Aspergillus niger*, or *Aspergillus oryzae* polypeptide.

In a more preferred aspect, the polypeptide is an *Aspergillus niger* polypeptide, e.g., the polypeptide of SEQ ID NO: 5.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.
Polynucleotides The present invention also relates to isolated polynucleotides having a nucleotide sequence which encode a polypeptide of the present invention. In a preferred aspect, the nucleotide sequence is set forth in SEQ ID NO: 4. In another preferred aspect, the nucleotide sequence is the mature polypeptide coding region of SEQ ID NO: 4. The present invention also encompasses nucleotide sequences which encode a polypeptide having the amino acid sequence of SEQ ID NO: 5 or the mature polypeptide thereof, which differ from SEQ ID NO: 4 by virtue of the degeneracy of the genetic code. The present invention also relates to subsequences of SEQ ID NO: 4 which encode fragments of SEQ ID NO: 5 that have protease activity.

The present invention also relates to mutant polynucleotides comprising at least one mutation in the mature polypeptide coding sequence of SEQ ID NO: 4, in which the mutant nucleotide sequence encodes a polypeptide which consists of amino acids 2 to 148 of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Aspergillus*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 4 (i.e., nucleotides 4 to 518) of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 4, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, Protein Expression and Purification 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for protease activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

The present invention also relates to isolated polynucleotides encoding a polypeptide of the present invention, which hybridize under medium stringency conditions, more preferably medium-high stringency conditions, even more preferably high stringency conditions, and most preferably very high stringency conditions with nucleotides 4 to 518 of SEQ ID NO: 4, a complementary strand thereof; or allelic variants and subsequences thereof (Sambrook et al., 1989, supra), as defined herein.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP),

*Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, Gene 98:61-67; Cullen et al., 1987, Nucleic Acids Research 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa,* or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Aspergillus*, and more preferably *Aspergillus niger* or *Aspergillus oryzae*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the mature polypeptide coding region of SEQ ID NO: 4, wherein the mutant nucleotide sequence encodes a polypeptide which consists of amino acids 2 to 148 of SEQ ID NO: 5, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Plants

The present invention also relates to a transgenic plant, plant part, or plant cell which has been transformed with a nucleotide sequence encoding a polypeptide having protease activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, Plant Physiology 86: 506.

For constitutive expression, the 35S-CaMV, the maize ubiquitin 1, and the rice actin 1 promoter may be used (Franck et al., 1980, Cell 21: 285-294, Christensen et al., 1992, Plant Mo. Biol. 18: 675-689; Zhang et al., 1991, Plant Cell 3: 1155-1165). Organ-specific promoters may be, for example, a promoter from storage sink tissues such as seeds, potato tubers, and fruits (Edwards & Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991-1000, the chlorella virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a polynucleotide encoding a polypeptide having protease activity of the present invention under conditions conducive for production of the polypeptide; and (b) recovering the polypeptide.

Removal or Reduction of Protease Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred embodiment, the nucleotide sequence is disrupted with a selectable marker such as those described herein.

Alternatively, modification or inactivation of the nucleotide sequence may be performed by established anti-sense techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. It has been found that a higher yield of homologous and/or heterologous polypeptides expressed in a host cell deficient for the protease according to the invention may be obtained, compared to the corresponding yield in same host cell but having normal level of the protease of the invention. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

It has been found that the polypeptide of the invention is responsible for cleaving off the CBM (Carbohydrate binding Module) of at least some polypeptides comprising two or more domains of which one domain is the CBM. Thus, in a further aspect the present invention relates to a method for producing a protein product comprising a polypeptide comprising two or more domains of which one domain is a CBM by fermentation of a cell having reduced expression of the polypeptide of the invention, which cell produces said polypeptide comprising two or more domains, and recovering the produce from the fermentation broth, and optionally subjecting the recovered product to further purification.

In a further aspect, the present invention relates to a method for producing a protein product essentially free of the protease activity of the polypeptide of the invention by fermentation of a cell which produces both a polypeptide of the present invention as well as the protein product of interest by adding an effective amount of an agent capable of inhibiting the protease activity of the polypeptide of the invention to the fermentation broth before, during, or after the fermentation has been completed, recovering the product of interest from the fermentation broth, and optionally subjecting the recovered product to further purification.

In a further aspect, the present invention relates to a method for producing a protein product essentially free of the protease activity of the polypeptide of the invention by cultivating the cell under conditions permitting the expression of the product, subjecting the resultant culture broth to a combined pH and temperature treatment so as to reduce the protease activity of the polypeptide of the invention substantially, and recovering the product from the culture broth. Alternatively, the combined pH and temperature treatment may be performed on an enzyme preparation recovered from the culture broth. The combined pH and temperature treatment may optionally be used in combination with a treatment with a protease inhibitor.

In accordance with this aspect of the invention, it is possible to remove at least 60%, preferably at least 65%, preferably at least 70%, preferably at least 75%, preferably at least 80%, preferably at least 85%, preferably at least 90%, preferably at least 95%, preferably at least 96%, more preferably at least 97%, even more preferably at least 98% and most preferably at least 99% of the protease activity of the polypeptide of the invention.

The methods used for cultivation and purification of the product of interest may be performed by methods known in the art.

The methods of the present invention for producing an essentially protease-free product or a product comprising a polypeptide comprising two or more domains of which one domain is a CBM wherein the amount of said polypeptide without the CBM is considerably low is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The protease-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from protease activity which is produced by a method of the present invention.

Compositions

The present invention also relates to compositions comprising a polypeptide of the present invention. Preferably, the compositions are enriched in such a polypeptide. The term "enriched" indicates that the protease activity of the composition has been increased, e.g., with an enrichment factor of 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having protease activity.

Detergent Compositions

The enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274—make references to specific sequences and positions.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).
Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).
Amylases: Suitable amylases (α and/or β) include those of bacterial or fungal origin. Chemically modified or protein engineered mutants are included. Amylases include, for example, α-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444—make references to specific sequences and positions.

Commercially available amylases are Duramyl™, Termamyl™, Fungamyl™ and BAN™ (Novozymes A/S), Rapidase™ and Purastar™ (from Genencor International Inc.).
Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 1999/001544.

Commercially available cellulases include Celluzyme™, and Carezyme™ (Novozymes A/S), Clazinase™, and Puradax HA™ (Genencor International Inc.), and KAC-500 (B)™ (Kao Corporation).
Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202 which is hereby incorporated as reference.

The present invention is further described by the following examples which should not be construed as limiting the scope of the invention.

EXAMPLES

Chemicals used as buffers and substrates were commercial products of at least reagent grade.
Media and Solutions
  Methods
  Unless otherwise stated, DNA manipulations and transformations were performed using standard methods of molecular biology as described in Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology", John Wiley and Sons, 1995; Harwood, C. R., and Cutting, S. M. (eds.) "Molecular Biological Methods for *Bacillus*". John Wiley and Sons, 1990.
  Enzymes
  Enzymes for DNA manipulations (e.g. restriction endonucleases, ligases etc.) are obtainable from New England Biolabs, Inc. and were used according to the manufacturer's instructions.
  Microbial Strains
  *E. coli* DH5α (TOYOBO)
  The used *Aspergillus niger* strain was a descendent from an original isolate C40, isolated by Novozymes from a soil sample collected in Copenhagen, Denmark.

*A. oryzae* BECh-2 is described in WO 2006/069289 (Novozymes).
  Media and Reagents
  Cove: 342.3 g/L Sucrose, 20 ml/L COVE salt solution, 10 mM Acetamide, 30 g/L noble agar.
  Cove salt solution: per liter 26 g KCl, 26 g $MgSO_4$-7 aq, 76 g $KH_2PO_4$, 50 ml Cove trace metals.
  Cove trace metals: per liter 0.04 g $NaB_4O_7$-10 aq, 0.4 g $CuSO_4$-5 aq, 1.2 g $FeSO_4$-7 aq, 0.7 g $MnSO_4$-aq, 0.7 g $Na_2MoO_2$-2 aq, 0.7 g $ZnSO_4$-7 aq.
  YPG: 4 g/L Yeast extract, 1 g/L $KH_2PO_4$, 0.5 g/L $MgSO_4$-7 aq, 5 g/L Glucose, pH 6.0.
  STC: 0.8 M Sorbitol, 25 mM Tris pH 8, 25 mM $CaCl_2$.
  STPC: 40% PEG4000 in STC buffer.
  Cove top agarose: 342.3 g/L Sucrose, 20 ml/L COVE salt solution, 10 mM Acetamide, 10 g/L low melt agarose.
  MS-9: per liter 30 g soybean powder, 20 g glycerol, pH 6.0.
  MDU-pH5: per liter 45 g maltose-1 aq, 7 g yeast extract, 12 g $KH_2PO_4$, 1 g $MgSO_4$-7 aq, 2 g $K_2SO_4$, 0.5 ml AMG trace metal solution and 25 g 2-morpholinoethanesulfonic acid, pH 5.0.

Example 1

Semi-Purification of *A. niger* 19 kDa Protease

Preparation of the Enzyme Sample
*A. niger* cells were freeze dried and kept at 4° C. 10 g of freeze dried cells were frozen by liquid $N_2$ and crushed by Ball Mill (stainless steel, volume 420 ml, Irie Syoukai Co. Ltd.), then homogenized by Physcotron (Microtec Nichion Co. Ltd.) in liquid $N_2$. The homogenate was suspended in 120 ml of 20 mM Tris-HCl, pH 7.5. After centrifugation, the precipitate was re-suspended in 120 ml of the same buffer and centrifuged again. Two supernatants were combined and filtered through a membrane filter (0.2 micrometer pore size). The filtrate was diafiltrated against the same buffer, resulting in 151.5 ml of crude enzyme sample.

Preparation of the Bacitracin Affinity Gel
Reagent:
Epoxy-activated Sepharose 6B (Amersham Biosciences, 17-0480-01)
Coupling buffer (50 mM $Na_2B_4O_7$—HCl, pH9)
Bacitracin (Wako Pure Chemical Industry Ltd., 022-07701, Lot EWM1905)
Procedure:
15 g of Epoxy-activated Sepharose 6B were suspended and washed with Milli-Q water according to the manufacturer's instructions.
Then the gel was washed with 200 ml of coupling buffer and filtered on a glass filter.
The gel cake was transferred to a sealed bottle with 50 ml coupling buffer.
2.5 g Bacitracin were dissolved in 50 ml of coupling buffer and mixed with the gel.
The reaction mixture was shaken gently at 25° C. overnight.
Wash away excess ligand using coupling buffer.
Block remaining active groups by 0.1M ethanol amine, pH 9 for 5 hrs at 25° C.
Wash with Coupling Buffer
Wash with 20 mM immidazole buffer, pH 6.5, containing 1 M NaCl and 25% iso-Propanol Purification of Proteases from *A. niger* by Bacitracin Affinity Column Column size: 22×100 mm
Flow rate: 4 ml/min
Fraction size: 8 ml/min The column was pre-equilibrated with 20 mM Tris-HCl, pH 7.5. 150 ml of crude enzyme sample was applied to the column. The column was washed with 170 ml of the same buffer, then 120 ml of the same buffer containing 1M NaCl. Proteases bound to the column were eluted by 120 mM of 1 M NaCl, and 25% iso-Propanol in the Tris buffer. The fractions that exhibit UV absorption were pooled and diafiltrated against the Tris-HCl buffer to remove NaCl and iso-Propanol. 56 ml of pooled fractions were concentrated to 0.6 ml by ultrafiltration.

SDS-PAGE

SDS-PAGE was performed in combination of Compact PAGE, AE7300 and pre-cast gel c-PAGEL, 12.5%, 76 mm (W)×70 mm (H) (ATTO Co.). Running buffer and SDS buffer were prepared by following ATTO's instruction manual. After electrophoresis, the gel was stained by SYPRO Orange protein gel stain (Invitrogen Co.). For identification of protease activity, 2-Mercaptoethanol was removed from SDS-buffer and boiling step of the sample was skipped. The gel was over-laid by 1% skim milk and 2% agarose dissolved in 50 mM Tris-HCl, pH 7.5.

The SDS-PAGE Gel is Shown in FIG. 1
lane 1: LMW Marker (97, 66, 45, 30, 20, 14.4 kDa, GE Healthcare))
lane 2: Purified Proteases (Boiled)
lane 3: Purified Proteases (without boiling and 2-Mercaptoethanol)
Skim milk-agarose over lay The patterns of SDS-PAGE with and without boiling samples were differed. The semi-purified sample was applied to an N-terminal sequencing analysis.

Example 2

De Novo Protein Sequencing

Partial amino acid sequence of the 19 kDa protease was obtained by N-terminal sequencing. For sample preparation a sample, semi-purified using the Bacitracin affinity column, was precipitated with TCA, separated on SDS-PAGE and blotted to a PVDF membrane. For N-terminal amino acid sequencing a piece of the PVDF membrane loaded with the 19 kDa band was cut out and placed in the blotting cartridge of an Applied Biosystems Procise protein sequencer. The N-terminal sequencing was carried out using the method run file for PVDF membrane samples (Pulsed liquid PVDF), in accordance with the manufacturer instructions. The following N-terminal sequence was obtained (one-letter code):

SPIPSYSRPGRG          (SEQ ID NO: 1)

Example 3

Cloning and Sequencing of *A. niger* 19 kDa Protease Gene

Based on the partial amino acid sequences and molecular weight identified by SDS-PAGE, the database search (JGI *A. niger* genome browser) was conducted and the following hit was obtained.

```
erseqn:zy163155 XSCFFLD1. Aspergillus niger
genomic sequence
Length =  3970925
Score =   30.0 bits (66), Expect =  0.98
Identities =  12/12 (100%),
Positives =  12/12 (100%)
Frame =  +1
Query:            1         SPIPSYSRPGRG           12
                            SPIPSYSRPGRG
Sbjct:      3509032         SPIPSYSRPGRG       350906
```

The following primers HU941 and HU942 which introduce a BamHI and an XhoI site, respectively, were designed based on the nucleotide sequences information of the *A. niger* genome database.

```
HU941:
TTTGGATCCACCATGTCCCCAATCCCCAGC  (SEQ ID NO: 2)

HU942:
TTTCTCGAGTCACCCCAAGAAAACATCCAC  (SEQ ID NO: 3)
```

A PCR reaction with the genome DNA of the *Aspergillus niger* strain as template was performed with an Expand™ PCR system (Roche Diagnostics, Japan) using HU941 and HU942. The amplification reactions (50 μl) were composed of 1 ng of template DNA per μl, 250 mM dNTP each, 250 nM primer HU941, 250 nM primer HU942, 0.1 U of Taq polymerase per μl in 1× buffer (Roche Diagnostics, Japan). The reactions were incubated in a DNA Engine PTC-200 (MJ-Research, Japan) programmed as follows: 1 cycle at 94° C. for 2 minutes; 30 cycles each at 92° C. for 1 minute, 55° C. for 1 minute, and 72° C. for 1 minute; 1 cycle at 72° C. for 10 minutes; and a hold at 4° C.

The reaction products were isolated on a 1.0% agarose gel using TAE buffer where a 0.5 kb product band was excised from the gel and purified using a QIAquick™ Gel Extraction Kit (QIAGEN Inc., Valencia, Calif.) according to the manufacturer's instructions.

The 0.5 kb amplified DNA fragment was digested with BamHI and XhoI, and ligated into the *Aspergillus* expression cassette pCaHj483 digested with BamH I and XhoI. The ligation mixture was transformed into *E. coli* DH5α (TOYOBO) to create the expression plasmid pHUda772. The amplified plasmid was recovered using a QIAprep® Spin Miniprep kit (QIAGEN Inc., Valencia, Calif.) according to the manufacturer's instructions.

Plasmid pCaHj483 comprised an expression cassette based on the *Aspergillus niger* neutral amylase II promoter fused to the *Aspergillus nidulans* triose phosphate isomerase non translated leader sequence (Na2/tpi promoter) and the *Aspergillus niger* amyloglycosidase terminator (AMG terminator), the selective marker amdS from *Aspergillus nidulans* enabling growth on acetamide as sole nitrogen source.

The resultant plasmid was sequenced and compared to the *Aspergillus niger* genome database, showing that clones encode the unknown 19 kDa protease. The cloned DNA sequences and its deduced amino acid sequences by predicting the introns (by NetGene 2) and results of the homology search based on the amino acid sequences.

The sequence of the *Aspergillus niger* 19 kDa gene and deduced amino acid sequence is shown in FIG. 2.

Results of the Homology Search

| Database: uniprot_trembl Program: blastp | | |
|---|---|---|
| Id | E | Description |
| a2q7n9 | 5e−82 | Similarity to hypothetical protein encoded by slr0318 - *Synechocystis* sp. |
| q2u3f4 | 5e−35 | Predicted protein. |
| a2qz06 | 3e−31 | Similarity to hypothetical protein encoded by slr0318 - *Synechocystis* sp. |
| q2u1v3 | 2e−19 | Predicted protein. |
| q5axc1 | 6e−18 | Hypothetical protein. |
| q4w9x2 | 2e−16 | L-PSP endoribonuclease family protein, putative. |
| a1d9u3 | 1e−15 | L-PSP endoribonuclease family protein, putative. |
| a2qyq7 | 1e−14 | Function: Mmf1p influences the maintenance of mitochondrial DNA. |
| q55925 | 1e−12 | Slr0318 protein. |
| q68e49 | 2e−12 | Endoribonuclease L-psp family protein. |
| a0r468 | 6e−12 | Endoribonuclease L-psp family protein. |
| a2qti5 | 1e−11 | Contig An09c0050, complete genome. |
| q5aqu2 | 2e−11 | Hypothetical protein. |
| a0ywm9 | 5e−11 | Endoribonuclease L-PSP. |
| q5arf7 | 1e−10 | Hypothetical protein. |
| q3m1g1 | 2e−10 | Endoribonuclease L-PSP. |
| q5b5q5 | 1e−09 | Hypothetical protein. |
| q2h829 | 2e−09 | Hypothetical protein. |
| q2u1l1 | 2e−08 | Predicted protein. |
| a4qwk3 | 1e−07 | Hypothetical protein. |
| q0mf29 | 4e−04 | Hypothetical protein. |
| q46me6 | 5e−04 | Endoribonuclease L-PSP. |
| q8xes9 | 5e−04 | Hypothetical transmembrane protein (Hypothetical protein). |
| q1lgu9 | 6e−04 | Endoribonuclease L-PSP. |
| q0kde1 | 6e−04 | Putative translation initiation inhibitor, yjgF family. |

None of the hits in the homology search revealed a polypeptide that has been identified as having protease activity.

Example 4

Expression of *A. niger* 19 kDa Protease Gene in *A. oryzae*

*Aspergillus oryzae* strain BECh-2 was inoculated to 100 ml of YPG medium and incubated for 16 hrs at 32° C. at 80 rpm. Pellets were collected and washed with 0.6 M KCl, and resuspended 20 ml 0.6 M KCl containing a commercial β-glucanase product (GLUCANEX™, Novozymes A/S, Bagsvrd, Denmark) at a final concentration of 600 μl per ml. The suspension was incubated at 32° C. and 80 rpm until protoplasts were formed, and then washed twice with STC buffer. The protoplasts were counted with a hematometer and resuspended and adjusted in an 8:2:0.1 solution of STC:STPC:DMSO to a final concentration of $2.5 \times 10^7$ protoplasts/ml.

Approximately 3 μg of pHUda772 was added to 100 μl of the protoplast suspension, mixed gently, and incubated on ice for 20 minutes. One ml of SPTC was added and the protoplast suspension was incubated for 30 minutes at 37° C. After the addition of 10 ml of 50° C. COVE top agarose, the reaction was poured onto COVE agar plates and the plates were incubated at 32° C. After 5 days transformants were selected from the COVE medium.

Four randomly selected transformants were inoculated into 100 ml of MS-9 medium and cultivated at 32° C. for 1 day. Three ml of MS-9 medium was inoculated into 100 ml of MDU-pH5 medium and cultivated at 30° C. for 3 days.

The grown mycelia was resuspended with SDS sample buffer and heated at 100° C. for 10 min. After centrifugation at 12,000 rpm for 10 min, the supernatants were recovered and applied to SDS-PAGE analysis (Compact PAGE, AE7300 and pre-cast gel c-PAGEL, 12.5%, 76 mm (W)×70 mm (H) (ATTO Co.). Sample buffer, Running buffer and SDS buffer were prepared by following ATTO's instruction manual. After electrophoresis, the gel was stained by SYPRO Orange protein gel stain (Invitrogen Co.). One of the 19 kDa protease expressing clones, strain 772-10, was selected for further experiments.

Example 5

Sample Preparation of the Expressed 19 kDa Protease

One of the selected transformants expressing *A. niger* 19 kDa protease intracellulary were grown under the conditions disclosed in example 4, mycelium was collected and lyophilized.

One gram of the lyophilized cell was grinded by a mortar and suspended in 25 ml of 10 mM phosphate buffer, pH 6.7 containing 0.5 M NaCl. Cell free extract was obtained by centrifugation. The cell free extract was concentrated to 4 ml and applied to HiLoad 26/60 Superdex 200 column (GE healthcare) pre-equilibrated by the same buffer. The sample was eluted by the same buffer (flow rate; 2 ml/min, fraction size 4 ml/2 min/fr). The chromatogram for the gel permeation is shown in FIG. 3.

SDS-PAGE was performed in combination of Compact PAGE, AE7300 and pre-cast gel c-PAGEL, 15%, 76 mm (W)×70 mm (H) (ATTO Co.). Running buffer and SDS buffer were prepared by following ATTO's instruction manual. After electrophoresis, the gel was stained by SYPRO Orange protein gel stain (Invitrogen Co.). (see FIG. 4)

Fractions 55, 56, 57 that containing the 19 kDa protease were pooled and used for further analysis.

Example 6

Characterization of the Expressed 19 kDa Protease

Substrate Specificity of the 19 kDa Protease

Five synthetic substrates were purchased from Peptide Institute Co., Osaka. The substrates are Glt-AAF-MCA, Suc-LLVY-MCA, Boc-FSR-MCA, Suc(OMe)-AAPV-MCA, and Z-LLE-MCA. 25 μl of 0.04 mM substrates were preincubated at 37° C. for 5 min. 20 μl of protease sample were mixed with 25 μl of 400 mM phosphate buffer, pH 6.7, 5 μl of 2 M NaCl, and 25 μl of Milli Q water, and then preincubated at 37° C. for 5 min. The reactions were started by mixing the substrate solutions and the enzyme solutions. Increases of fluorescent strength were measured by FL600 Microplate Fluorescence Reader with 360 nm excitation and 460 nm emission filters at 37° C. for 30 min. Suc-LLVY-MCA is the best substrate.

| | |
|---|---|
| Glt-AAF-MCA | 1.6% |
| Suc-LLVY-MCA | 100.0% |
| Boc-FSR-MCA | 0.3% |
| Suc(OMe)-AAPV-MCA | 0.2% |
| Z-LLE-MCA | 0.1% |

Effects of Inhibitors 4-(2-aminoethyl)-benzenesulfonyl fluoride (AEBSF), leupeptin, pepstatin A, $ZnSO_4$, and EDTA were purchased from Wako Chemical Co., Osaka. The inhibitors were 4.5 mg/10 ml leupeptin in DMSO diluted 10 times by Milli Q water, 3 mg/10 ml pepstatin A in DMSO diluted 10 times by Milli-Q water, 10 mM AEBSF, 10 mM ZnSO$_4$, and 10 mM EDTA. The substrate was 0.04 mM Suc-LLVY-MCA. Enzyme solution contains 5 µl of pooled 19 kDa protease fraction, 10 µl of inhibitors, 25 µl of 400 mM KPB, pH6.7, and 35 µl of Milli-Q water. The substrate solution and the enzyme solutions were preincubated separately at 37° C. for 5 min. The activities were measured as described above.

|  | residual activity (%) |
|---|---|
| No inhibitor | 100 |
| Leupeptin | 89 |
| AEBSF | 100 |
| Pepstatin | 91 |
| ZnSO4 | 99 |
| EDTA | 101 |

No clear inhibition by any inhibitor was observed.
pH Profile

Phosphate buffer pH6, 7, 8, and Diethanolamine buffer pH8, 9, 10 were used. The substrate solution was 0.04 mM Suc-LLVY-MCA. The enzyme solution contains 5 µl of 19 kDa protease, 25 µl of buffer, 5 µL of 2 M NaCl and 40 µL of Milli Q water. Assay was performed as described before. The results are shown in FIG. 5. The 19 kDa protease is an alkaline protease with the pH optimum 8-9.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

---

The invention claimed is:

1. A recombinant or isolated cell, derived from a parent cell, wherein the parent cell comprises a protein comprising a protease having at least 95% sequence identity to 2 to 148 of SEQ ID NO: 5,
wherein the recombinant or isolated cell is produced by disrupting or deleting, in the parent cell, the nucleotide sequence encoding the parent cell protein, and
wherein, compared to the parent cell, the recombinant or isolated cell has reduced production of the protein comprising the protease having at least 95% sequence identity to 2 to 148 of SEQ ID NO: 5.

2. The recombinant or isolated cell of claim 1, which further comprises a gene encoding a heterologous protein.

3. A recombinant cell, derived from a parent cell, wherein the parent cell comprises a protein comprising a protease having at least 95% sequence identity to 2 to 148 of SEQ ID NO: 5,
wherein the recombinant cell is produced by disrupting or deleting, in the parent cell, the nucleotide sequence encoding the parent cell protein, and
wherein, compared to the parent cell, the recombinant cell has reduced production of the protein comprising the protease having at least 95% sequence identity to 2 to 148 of SEQ ID NO: 5.

4. The recombinant or isolated cell of claim 1, wherein the protease having at least 95% sequence identity to 2 to 148 of SEQ ID NO: 5 consists of the amino acid sequence 2 to 148 of SEQ ID NO: 5.

5. The recombinant or isolated cell of claim 1, wherein the protein comprising the protease having at least 95% sequence identity to 2 to 148 of SEQ ID NO: 5 consists of the amino acid sequence 2 to 148 of SEQ ID NO: 5.

6. The recombinant cell of claim 3, which further comprises a gene encoding a heterologous protein.

7. The recombinant cell of claim 3, wherein the protease having at least 95% sequence identity to 2 to 148 of SEQ ID NO: 5 consists of the amino acid sequence 2 to 148 of SEQ ID NO: 5.

8. The recombinant cell of claim 3, wherein the protein comprising the protease having at least 95% sequence identity to 2 to 148 of SEQ ID NO: 5 consists of the amino acid sequence 2 to 148 of SEQ ID NO: 5.

* * * * *

SEQUENCE LISTING

```
<160> NUMBER OF SEQ ID NOS: 5

<210> SEQ ID NO 1
<211> LENGTH: 12
<212> TYPE: PRT
<213> ORGANISM: Aspergillus niger

<400> SEQUENCE: 1

Ser Pro Ile Pro Ser Tyr Ser Arg Pro Gly Arg Gly
1               5                   10

<210> SEQ ID NO 2
<211> LENGTH: 30
<212> TYPE: DNA
<213> ORGANISM: Artificial Sequence
<220> FEATURE:
<223> OTHER INFORMATION: Primer HU941

<400> SEQUENCE: 2
tttggatcca ccatgtcccc aatccccagc                                      30

<210> SEQ ID NO 3
<211> LENGTH: 30
<212> TYPE: DNA
<213> ORGANISM: Artificial Sequence
<220> FEATURE:
<223> OTHER INFORMATION: Primer HU942

<400> SEQUENCE: 3
tttctcgagt cacccccaaga aaacatccac                                     30

<210> SEQ ID NO 4
<211> LENGTH: 518
<212> TYPE: DNA
<213> ORGANISM: Aspergillus niger
<220> FEATURE:
<221> NAME/KEY: CDS
<222> LOCATION: (1)..(112)
<220> FEATURE:
<221> NAME/KEY: CDS
<222> LOCATION: (184)..(515)

<400> SEQUENCE: 4
```

```
atg tcc cca atc ccc agc tac tcc cgc ccc ggc cgc ggc caa cac ttc        48
Met Ser Pro Ile Pro Ser Tyr Ser Arg Pro Gly Arg Gly Gln His Phe
1               5                   10                  15 caa gat gcc tac ggc ttc gcc gaa gcc tgc ata gcc gga gac cga atg        96
Gln Asp Ala Tyr Gly Phe Ala Glu Ala Cys Ile Ala Gly Asp Arg Met
                20                  25                  30 gaa ata gcc ggc cag a gtgagccacc atctcctttc cctccatttc cctcatcacc     152
Glu Ile Ala Gly Gln
            35 aactaatcca atccccccct caacaaacta g cc  ggc atg tcc ccc aca tca        203
                                     Thr Gly Met Ser Pro Thr Ser
                                                 40 acc gaa gtc cca ccc acc ctc gaa gaa gaa gtc gcg caa gca ttc aac       251
Thr Glu Val Pro Pro Thr Leu Glu Glu Glu Val Ala Gln Ala Phe Asn
45                  50                  55                  60 aac atc aac gaa gtt atc ctc tac aca cta gag aaa gcc aag ccc gat       299
Asn Ile Asn Glu Val Ile Leu Tyr Thr Leu Glu Lys Ala Lys Pro Asp
                65                  70                  75 ctg cgc gct agc gtc aag agc ggc tgg gac cgc gtc gtg aag atc cgc       347
Leu Arg Ala Ser Val Lys Ser Gly Trp Asp Arg Val Val Lys Ile Arg
                80                  85                  90 acg tac cat gtc cag ttg ccc cag acc cgg gag aag att atc ggc cta       395
Thr Tyr His Val Gln Leu Pro Gln Thr Arg Glu Lys Ile Ile Gly Leu
                95                  100                 105 atg gta gag aat gtt aag aag tgg tgt ccg gat cat cag cct act tgg       443
Met Val Glu Asn Val Lys Lys Trp Cys Pro Asp His Gln Pro Thr Trp
            110                 115                 120 act atg ttg ggg att gag gcc ttg ccg ttt gaa ggg cag aat ttg gag       491
Thr Met Leu Gly Ile Glu Ala Leu Pro Phe Glu Gly Gln Asn Leu Glu
125                 130                 135                 140 att gag gtg gat gtt ttc ttg ggg tga                                   518
Ile Glu Val Asp Val Phe Leu Gly
                145

<210> SEQ ID NO 5
<211> LENGTH: 148
<212> TYPE: PRT
<213> ORGANISM: Aspergillus niger

<400> SEQUENCE: 5

Met Ser Pro Ile Pro Ser Tyr Ser Arg Pro Gly Arg Gly Gln His Phe
1               5                   10                  15

Gln Asp Ala Tyr Gly Phe Ala Glu Ala Cys Ile Ala Gly Asp Arg Met
                20                  25                  30

Glu Ile Ala Gly Gln Thr Gly Met Ser Pro Thr Ser Thr Glu Val Pro
            35                  40                  45

Pro Thr Leu Glu Glu Glu Val Ala Gln Ala Phe Asn Asn Ile Asn Glu
        50                  55                  60

Val Ile Leu Tyr Thr Leu Glu Lys Ala Lys Pro Asp Leu Arg Ala Ser
65                  70                  75                  80

Val Lys Ser Gly Trp Asp Arg Val Val Lys Ile Arg Thr Tyr His Val
                85                  90                  95

Gln Leu Pro Gln Thr Arg Glu Lys Ile Ile Gly Leu Met Val Glu Asn
            100                 105                 110

Val Lys Lys Trp Cys Pro Asp His Gln Pro Thr Trp Thr Met Leu Gly
        115                 120                 125
```

```
Ile Glu Ala Leu Pro Phe Glu Gly Gln Asn Leu Glu Ile Glu Val Asp
    130                 135                 140

Val Phe Leu Gly
145
```